(12) United States Patent
Dubey et al.

(10) Patent No.: US 10,525,162 B2
(45) Date of Patent: Jan. 7, 2020

(54) SOPHOROLIPID MEDIATED ACCELERATED GELATION OF SILK FIBROIN

(71) Applicant: COUNCIL OF SCIENTIFIC & INDUSTRIAL RESEARCH, New Delhi (IN)

(72) Inventors: Parul Dubey, Maharashtra (IN); Philem Pushparani Devi, Maharashtra (IN); Anuya Amol Nisal, Maharashtra (IN); Asmita Ashutosh Prabhune, Maharashtra (IN)

(73) Assignee: Council of Scientific & Industrial Research, New Delhi (IN)

( * ) Notice: Subject to any disclaimer, the term of this patent is extended or adjusted under 35 U.S.C. 154(b) by 215 days.

(21) Appl. No.: 15/309,352

(22) PCT Filed: May 8, 2015

(86) PCT No.: PCT/IN2015/000200
§ 371 (c)(1),
(2) Date: Nov. 7, 2016

(87) PCT Pub. No.: WO2015/170342
PCT Pub. Date: Nov. 12, 2015

(65) Prior Publication Data
US 2017/0056551 A1    Mar. 2, 2017

(30) Foreign Application Priority Data
May 9, 2014 (IN) .......................... 1248/DEL/2014

(51) Int. Cl.
| | | |
|---|---|---|
| *A61L 27/00* | (2006.01) | |
| *A61L 27/22* | (2006.01) | |
| *A61L 27/52* | (2006.01) | |
| *A61L 27/56* | (2006.01) | |
| *A61L 27/54* | (2006.01) | |
| *A61L 27/36* | (2006.01) | |

(52) U.S. Cl.
CPC ............. *A61L 27/227* (2013.01); *A61L 27/00* (2013.01); *A61L 27/3604* (2013.01); *A61L 27/52* (2013.01); *A61L 27/54* (2013.01); *A61L 27/56* (2013.01); *A61L 2300/22* (2013.01); *A61L 2300/232* (2013.01)

(58) Field of Classification Search
CPC .......... A61L 27/00; A61L 27/52; A61L 27/54; A61L 27/56; A61L 27/227; A61L 27/3604; A61L 2300/22; A61L 2300/232
USPC ......................................................... 514/25
See application file for complete search history.

(56) References Cited

U.S. PATENT DOCUMENTS 5,981,497 A * 11/1999 Maingault ................ A61K 8/60
514/25

FOREIGN PATENT DOCUMENTS

| WO | WO 2005/012606 A2 * | 2/2005 | |
| WO | WO 2013/112875 A1 | 8/2013 | |
| WO | WO 2013/163407 A1 * | 10/2013 | ............. A61K 47/42 |

OTHER PUBLICATIONS

International Search Report (ISR) for PCT/IN2015/000200; I.A. fd: May 8, 2015, dated Sep. 1, 2015, European Patent Office, Rijswijk, Netherlands.
International Preliminary Report on Patentability (IPRP) including the Written Opinion of the International Searching Authority (PCT Rule 44bis) for PCT/IN2015/000200; I.A. fd: May 8, 2015, dated Nov. 15, 2016, by the International Bureau of WIPO, Geneva, Switzerland.
Wu, X et al.,"Sodium dodecyl sulfate-induced rapid gelation of silk fibroin," Acta Biomater. Jul. 2012;8(6):2185-92. doi: 10.1016/j.actbio.2012.03.007. Epub Mar. 9, 2012.

* cited by examiner

*Primary Examiner* — Ganapathy Krishnan
(74) *Attorney, Agent, or Firm* — Sterne, Kessler, Goldstein & Fox P.L.L.C.

(57) ABSTRACT

The present invention provides a biocompatible hydrogel composition comprising glycolipids and silk fibroin (SF) wherein glycolipid is preferably sophorolipids (SL). The said composition is useful in preparation of 3D scaffold for use in tissue engineering, and in the biomedical field. The present invention also provides a process for preparing such a composition and a process for acceleration of gelation time of silk fibroin (SF) in the presence of sophorolipid.

13 Claims, 5 Drawing Sheets

SOPHOROLIPID MEDIATED ACCELERATED GELATION OF SILK FIBROIN

FIELD OF THE INVENTION

The present invention relates to field of biocompatible hydrogel compositions in general. More particularly, the present invention relates to a biocompatible hydrogel composition comprising silk fibroin and sophorolipids for use in biomedical applications such as implants, scaffolds in tissue engineering, wound dressings, drug delivery vehicles etc. The present invention also relates to a process for accelerating gelation of silk fibroin (SF), particularly in the presence of sophorolipids (SL).

BACKGROUND OF THE INVENTION

Silk fibroin (SF), derived from silkworm *Bombyx mori*, is a fibrous protein. It is extensively studied in biomedical field, due to inherent and unique biological properties such as biocompatibility, biodegradability, thermo-mechanical properties and minimum inflammatory reaction. SF can be processed in versatile forms such as thin films, sponges, composites, fibers, microspheres, non-woven mats, tubes and hydrogels.

Hydrogels are especially useful for several biomedical applications such as implants, scaffolds in tissue engineering, wound dressings, drug delivery vehicles and in vitro disease models. Hydrogels are a class of highly hydrated polymeric materials and can maintain a distinct 3D porous structure with mechanical and structural integrity similar to characteristics of many natural tissues and extra-cellular matrices. Silk fibroin solutions progressively undergo gelation if stored at physiological pH at room temperature. However, this process happens over a period of few days to months depending on concentration of solution used. This long gelation time of silk fibroin has been a barrier in its applications in the biomedical field (Kaplan et. al. 2012)

Factors affecting the silk fibroin gelation time such as pH, temperature, concentration of solution, accelerating agents have been subject matters of intense research leading to several patents as well as scientific publications. For SF solutions, gelation can also be induced by physical stimuli such as vortexing, sonication and electrical currents. However, these methods are non-physiological. Further, gelation of aqueous solution of SF depends strongly on the pH; it becomes highly unstable at pH near the isoelectric point of fibroin and is converted into macro-porous gels. Whereas, below the isoelectric pH, the gelation time varies between 10-16 hours and slightly above the isoelectric pH the gelation time increases dramatically and gelation occurs over a period of few days to weeks.

Several methods have been proposed and used for accelerating the gelation time of SF. There are reports prevalent in the art that suggest the use of additives such as polyethylene oxide (PEO), Pluronic (Poloxamer) and other polymeric additives as a gelling agent for silk fibroin to attain lower gelation time, under mild conditions. However PEO and Pluronic reduce the gelation time in limited fashion only. Kaplan et al in *Acta Biomaterialia* 8, 2185-2192 (2012) has proposed the use of Sodium do-decyl sulphate (SDS) for the accelerated gelation of silk. At low surfactant concentrations, hydrophobic interactions among the SF chains play a dominant role in the association, leading to decreased gelation time. At higher concentrations of surfactant, electrostatic repulsive forces among micellar aggregates gradually became dominant and gelation is hindered. These additives are still not ideal additives for forming biologically relevant hydrogels because of their chemical and non-biodegradable nature. Considering the various disadvantages and limitations of the prior art systems, the present inventors developed a novel composition comprising silk fibroin and sophorolipid which has not been reported anywhere before. It was surprisingly found by the present inventors that a biosurfactant like sophorolipid can accelerate the gelation of silk fibroin at physiological and alkaline pH.

OBJECTS OF THE INVENTION

The main object of the present invention is to provide a biocompatible hydrogel composition comprising glycolipids and silk fibroin (SF) and process for preparation thereof.

Another object of the present invention is to provide a process for accelerating gelation of silk fibroin (SF) by reducing gelation time of silk fibroin solution from weeks to few hours at physiological pH by employing a biosurfactant.

Yet another object of the present invention is to convert the silk fibroin-bio surfactant hydrogel into 3D-porous scaffold with tunable pore size and porosities such that they can find applications as implants in tissue engineering.

SUMMARY OF THE INVENTION

The present invention provides biocompatible hydrogel composition comprising glycolipids and silk fibroin (SF) wherein glycolipid is preferably sophorolipids (SL), preferably in the ratio ranging between 1:3 to 1.6:1. The said composition is useful in preparation of 3D scaffold for use in tissue engineering, and in the biomedical field. The present invention also provides a process for the preparation of hydrogel compositions.

BRIEF DESCRIPTION OF THE DRAWINGS

FIG. 8 depicts the cell imaging of cell laden SF-SL hydrogel scaffolds, wherein FIG. 8(a) depicts adherent cell morphology on scaffolds at 48 h post seeding and fixing with 2.5% glutaraldehyde using Floid® Cell Imaging System with fixed 20× Plan Fluorite objective having Image resolution—1296×964 pixels. Scale bar for all images is 100 μm; and FIG. 8(b) depicts confocal images of DAPI and Nile red stained L929 fibroblast cells and scaffold matrices.

DETAILED DESCRIPTION OF THE INVENTION

Figure 1A:
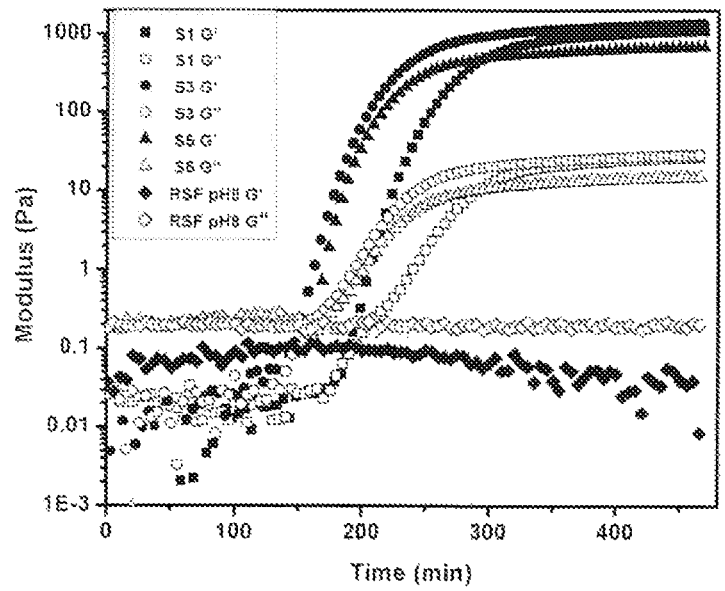
FIG. 1 (a) depicts the rheological study of SF-SL solutions at different SL concentrations at physiological pH to study the kinetics of gelation and 1(b) depicts the rheological study of SF+SL (30+30 mg/mL) to monitor kinetics of gelation at different pH.

Accordingly, the present invention provides biocompatible hydrogel composition comprising glycolipids and silk fibroin (SF) wherein glycolipid is preferably sophorolipids (SL). The said composition is useful in preparation of 3D scaffold for use in tissue engineering, and in the biomedical field. Thus, the present invention provides a biocompatible hydrogel composition comprising protein, preferably silk fibroin and a glycolipid, preferably sophorolipid, and more particularly oleic acid derived sophorolipid, said sophorolipid reduces the gelation time of silk fibroin. Further these hydrogels are lyophilized to obtain 3D porous scaffolds. The scaffolds constructed from hydrogel comprising of protein preferably silk fibroin and glycolipid bio surfactants preferably sophorolipid is studied for its mechanical properties and % beta sheets present in order to determine mechanical integrity and stability.

In an embodiment of the present invention, the ratio of glycoplipids and silk fibroin is the range of 1:3 to 1.6:1.

In an embodiment of the present invention, the pore size of the hydrogel composition is in the range of 20 to 200 μm.

In yet another embodiment of the present invention, the sophorolipid as used in the composition is selected from the group consisting of sophorose, oleic acid, linolenic acid, linoleic acid or stearic acid derived sophorolipids.

In yet another embodiment of the present invention, the concentration of silk fibroin in the composition is in the range of 3 g % to 5 g % preferably 3 g % (w/v).

In yet another embodiment of the present invention, the concentration of sophorolipid in the composition is in the range of 1 g to 5 g % w/v.

In yet another embodiment of the present invention, silk fibroin used in the composition is optionally regenerated silk fibroin (RSF).

In another embodiment of the present invention, the said composition is lyophilized to provide 3D SF-SL scaffolds.

In yet another embodiment of the present invention, the said composition is useful in preparation of 3D scaffold for use in tissue engineering, as implants and as dermal fillers.

The present invention also provides a process for the preparation of hydrogel compositions and the said process comprising the steps of:
 i. treating silk fibroin solution with sophorolipid in the ratio ranging between 3:1 to 1:1.6 at pH to obtain a mixture;
 ii. allowing the mixture as obtained in step (i) to stand till gelation for period in the range of 100 to 1000 minutes to obtain hydrogel composition.

In yet another embodiment of the present invention, the sophorolipid is selected from the group consisting of sophorose, oleic acid, linolenic acid, linoleic acid or stearic acid derived sophorolipids.

In yet another embodiment of the present invention, the concentration of silk fibroin is in the range of 3 g % to 5 g % preferably 3 g % (w/v).

In yet another embodiment of the present invention, the concentration of sophorolipid is in the range of 1 g to 5 g % w/v.

In yet another embodiment of the present invention, silk fibroin is optionally regenerated silk fibroin (RSF).

In yet another embodiment of the present invention, the process is performed in physiological conditions in pH ranging from 6 to 10, preferably at pH 8.

The biological materials employed in the instant invention may be used from the following but may not be limited to the following:
 Silk: *Bombyx mori*; procured from Central Seri cultural Research and Training Institute, Mysore, India.
 *Candida bombicola* (ATCC 22214)
 Mouse fibroblast cell line L929 (ATCC CCL-1)

According to another aspect of the invention, the present invention provides a process for the acceleration of gelation of silk fibroin (SF) by employing a glycolipid bio surfactant, preferably sophorolipid (SL). Further both the solutions (SF and SL) are mixed together gently and the clear solution so obtained is allowed to stand at room temperature till it gels.

According to another aspect of the invention, cell adhesion, cell proliferation and cytotoxicity assays are performed to determine the use of scaffolds in tissue engineering and in the biomedical field.

In one embodiment, in the process, regenerated silk fibroin (RSF) solution is optionally treated with sophorolipids to undergo gelation.

In yet another embodiment, 3% silk fibroin is treated with SL in the range of 1 to 5% w/v, to derive a clear solution having pH of about 7.4±0.2.

In yet another embodiment, the glycolipid used in this accelerated gelation process is preferably a sophorolipid selected from the group of hydrophillic glucose molecules and lipids selected from oleic, linoleic or stearic acid.

In yet another embodiment, the glycolipid is preferably a sophorolipid selected from the group consisting of sophorose and lipids selected from oleic, linolenic, linoleic or stearic acid.

In one embodiment, the sophorolipid bio-surfactant i.e. oleic acid derived sophorolipid is used as a gelling agent in the invention to accelerate the gelation process by reducing the gelation time. The SL used in the process is produced by non-pathogenic, GRAS certified yeast, *Candida bombicola* and is thereby biocompatible. The synthesis of oleic acid derived sophorolipid employed in the instant invention is disclosed in Asmer H-J, Lang S, Wagner F, Wray V (1988) *Microbial production, structure elucidation and bioconversion of sophorose lipids. J. Am. Oil Chem. Soc.* 65: 1460-1466. The hydrogel composition comprises biocompatible ingredients and may therefore be concluded to be biocompatible.

Figure 1B:
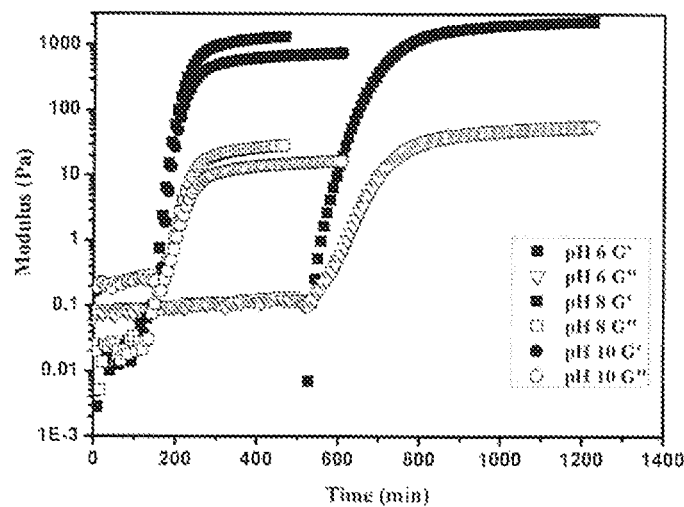

In order to confirm gelation of SF by the process, a simple test tube inverting test is performed i.e. the fluid in the tube does not flow upon inversion. Gel formation is further confirmed by detailed rheological studies. Reference to FIG. 1(b), indicate that gel formation is quickest at pH 8. On treating silk fibroin with SL at pH 8, the storage modulus G' of the SF+SL solution increases rapidly as compared to pH 6 and 10. Both G' and G" increase by orders of magnitude, with G'>G". The minimum gelation point is 140 min for SF+SL (30 mg/mL, pH 8) solution. The gelation time is also sensitive to the concentration of SL used and is found to be minimum when SL of 30 mg/mL is used (FIG. 1 (a)).

The gelation time of silk fibroin in the presence of sophorolipids is in the range of 100 minutes to 1000 minutes (FIG. 2) depending upon sophorolipid concentration and pH.

Figure 3:
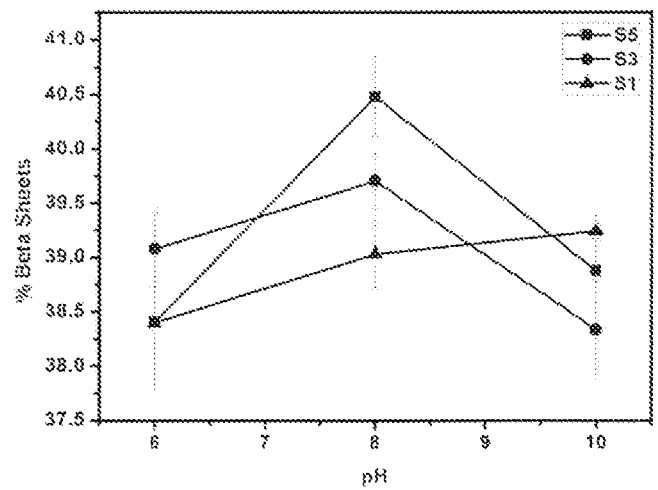
FIG. 3 depicts the % beta sheets of the scaffolds at varying SL pH and concentrations studied using IR spectroscopy.

FIG. 3 indicates highest β-sheets in the hydrogel at near physiological pH (pH 8), with highest concentration of SL (50 mg/mL), while at pH 6 and 10 beta sheet content was not found to be a function of SL concentration.

The SF-SL hydrogels formed can be lyophized to produce 3 D porous scaffolds, which can be useful for tissue engineering applications. Pore size of the SF-SL hydrogel produced by this accelerated gelation process as indicated in SEM micrographs is graphically defined in FIG. 4(a). Pore size is largest at pH 8, whereas pHs 6 and 10 have lower and comparable pore size. At near physiological pH (pH 8) pore size was observed to be inversely proportional to increasing SL concentration.

A study of the mechanical properties of the lyophilized scaffolds was carried out by determining the dry compression modulus. From FIG. 5, it can be noted that increase in SL concentrations results in lower compression modulus.

Cell adhesion, cell proliferation and cytotoxicity assays of cell laden hydrogel scaffold discs were also performed to determine the bio-compatibility of the SF-SL compositions using mouse fibroblast cell line L929 (ATCC CCL-1).

Thus, the present invention provides a hydrogel having tunable gelation time in the range of 100-1000 mins. The composition comprises SF and SL in the ratio in the range of 3:1 to 1:1.6. In yet another embodiment, the biocompatible hydrogel composition was lyophilized to obtain porous 3D SF-SL scaffolds with pore size in the range of 1 to 250 microns, porosity in the range of 90-93%, and dry compression modulus in the range of 0.1-3 MPa. The SF-SL hydrogel composition is synergistic and as 3D scaffolds provide excellent materials for use as biomaterials for implants, drug delivery, as dermal fillers, void fillers, as scaffolds in tissue engineering.

EXAMPLES

Following examples are given by way of illustration therefore should not be construed to limit the scope of the invention.

Example 1

Preparation of Regenerated Silk Fibroin

Regenerated silk fibroin solutions were prepared from bivoltine *Bombyx mori* cocoons that were procured from Central Seri cultural Research and Training Institute, Mysore, India. The cocoons were boiled in 0.05 w/v % of $NaHCO_3$ solution twice for 30 mins each to remove sericin. The extracted fibroin mass was then dissolved in 9.3 M Lithium Bromide (Sigma Aldrich) solution at 60° C. for 4 h. The solution was then extensively dialyzed for 48 h with at least 6 changes of water to ensure complete removal of the salt. This Regenerated Silk Fibroin (RSF) solution was adjusted to concentration of 30 mg/mL before use in all further experiments. The final concentration of the RSF solution after dialysis was determined by weighing the remaining solid of a known volume of RSF solution that was dried at 60° C. in a vacuum oven and was approximately indicated to be 5% (w/v). For the purposes of the instant invention 3% silk solution was prepared by diluting the 5% solution with deionized water. The pH of the regenerated silk solution was measured to be 6.9±0.2.

Example 2

Preparation of Sophorolipid Solution

Oleic acid derived sophorolipid was synthesized by supplementing *Candida bombicola* (ATCC 22214) using glucose and oleic acid employing the method described by Van Bogaert et al 2007. To study the effect of sophorolipid concentration on the gelation time of RSF solutions and thereafter to utilize the efficient concentrations of both the ingredients in a composition, oleic acid derived sophorolipid solutions were prepared at different concentrations i.e. 10, 30 and 50 mg/mL respectively. The pH of each concentration solution was set at 6, 8 and 10, using 0.1 N NaOH and then used for further experiments.

Example 3

Preparation of Hydrogels

Figure 2:
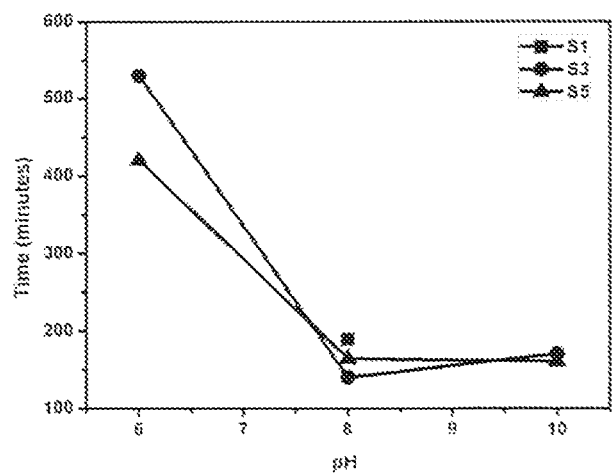
FIG. 2 depicts the gelation time of different concentrations of the SF-SL hydrogel at varying pH.

The silk fibroin solution prepared in Example 1 and sophorolipid solutions at different pH prepared in Example 2 were mixed in various ratios and allowed to stand till gelation. The prepared mixtures were characterized for their rheological properties. The experiment was started immediately after mixing the required quantities of SF solution into the pH adjusted SL solution. The cross-over of G' and G" was considered to be the gelation time (FIGS. 1a, b). Increasing concentration of SL in the mixture resulted in decrease in gelation time until a limit, beyond which further reduction in gelation time was not observed. Gelation at pH 6 was prolonged as compared to pH 8 and pH 10 (FIG. 2). The hydrogels obtained in Example 3 were further characterized for % beta sheets as a function of SL concentration.

FIG. 3 depicts that increasing SL concentration assisted in higher % beta sheets in the hydrogel.

Example 4

Preparation of SF-SL Scaffolds

The SF-SL solutions referred in Example 3 were allowed to gel in a 96 well cell culture plate at room temperature 25° C. The plate was lyophilized for at least 16 h, to obtain 3D porous scaffolds of SF-SL. The prepared scaffolds were then characterized by different techniques. The cross-sectional morphology of these 3D scaffolds was visualized using a scanning electron microscope. The hydrogels represented a continuous porous morphology (FIG. 4 b).

Porosity and Pore Size Measurements

The % porosity as calculated by liquid displacement method reported elsewhere (E. S. Gil, J. A. Kluge, D. N. Rockwood, R. Rajkhowa, L. Wang, X. Wang and D. L. Kaplan, *Journal of Biomedical Materials Research—Part A*, 2011, 99 A, 16-28.) was found to be 90±3% for all the scaffolds.

Figure 4A:
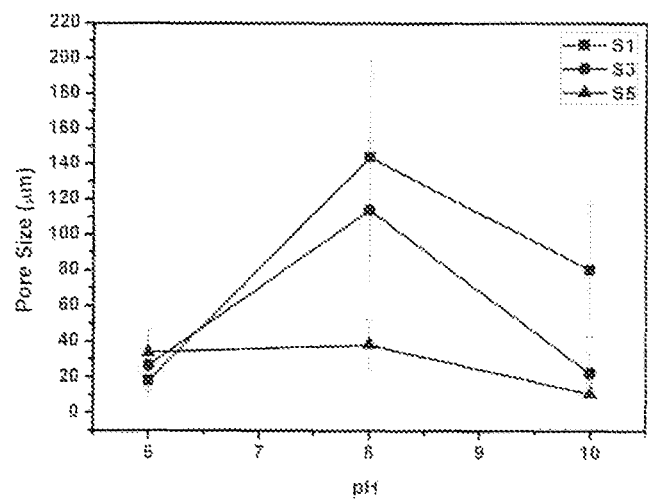
FIG. 4(a) depicts the pore size of SF-SL scaffolds at varying SL pH and concentrations and FIG. 4(b) depicts scanning electron micrographs of cut surface of lyophilized scaffolds for (a) SF+SL (30+10 mg/mL), (b) SF+SL (30+30 mg/mL) and (c) SF+SL (30+50 mg/mL) samples at pH 8. Scale bar for all images is 50 μm.
Figure 4B:
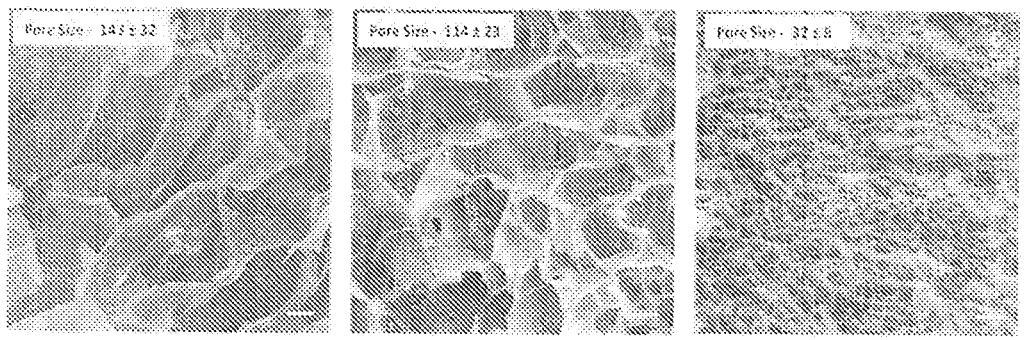

A trend in pore size was observed i.e., with increasing SL concentration at pH 8.0±0.2 from 10 mg/mL to 30 mg/mL to 50 mg/mL pore size decreased from 143±32 to 114±23 to 32±8 μm respectively (FIG. 4 b). Similar trend was observed in case of pH 10±0.2. Whereas at pH 6 the pore size at all the three concentrations of SL was comparable without much variation (FIG. 4a). The internal architecture of the hydrogels was dependent on SL concentration. This high porosity and large pore sizes in an important requisite of 3D scaffolds for tissue engineering applications to aid in easy transport of nutrients and cell migration.

Mechanical Analysis: Measurement of Dry Compression Modulus

Figure 5:
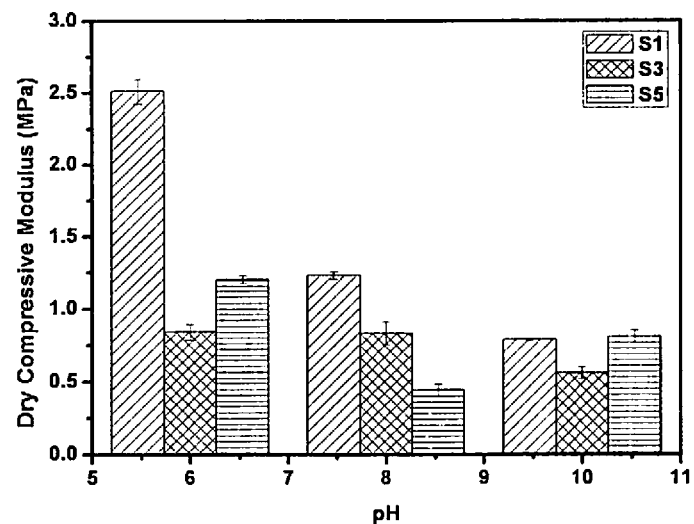
FIG. 5 depicts the dry compression modulus of the 3D scaffold prepared after lyophilizing the hydrogels obtained by varying SL pH and concentrations.

The scaffolds prepared in Example 4 were characterized for their dry compression modulus (FIG. 5). Addition of a small organic molecule like SL deteriorated the modulus of the scaffold. At pH 6.0±0.2 and pH 10.0±0.2 only a slight variation in dry compressive modulus with respect to SL concentration was observed. However, the measured compression moduli indicated that the mechanical integrity of these 3D structures is sufficient to be evaluated for tissue engineering applications.

Example 5

Cell Viability and Activity of Cell Laden SF-SL Scaffold

Figure 6:
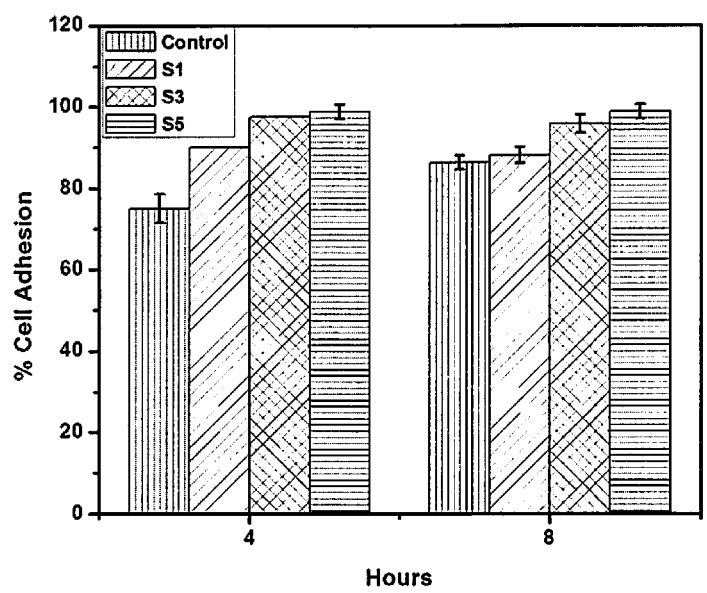
FIG. 6 depicts adhesion of mouse fibroblast (L929) cells as a function of time on lyophilized scaffolds prepared using hydrogels of SF+SL solutions (30+10 mg/mL; 30+30 mg/mL; 30+50 mg/mL) at pH 8.

The scaffold prepared in Example 4 were further analyzed for their capability to support adherence and proliferation of mouse fibroblast cell line L929 (ATCC CCL-1) obtained from National Center for Cell Science, Pune. The obtained scaffolds were sterilized and cells were seeded on them. The adhesion of mouse fibroblast to the SF-SL scaffolds was characterized after 4 and 8 h (FIG. 6). The porous structure of the scaffolds provides a 3D space with enhanced surface area thus increasing the available space for cells to adhere. This was proved by higher percentage adherence of cells to scaffolds in comparison to control polystyrene culture plates. Further, an increase in SL content resulted in minimal improvements in ability of the cells to attach to the scaffold. Not a very significant difference in % cell adhesion was found between the three samples, which well corroborated with the minor variation in % porosity of the scaffolds.

MTT assay was performed on scaffolds prepared in Example 4 to quantify proliferation of L929 fibroblast cells within the hydrogel constructs (scaffolds with cells) at intervals of 2, 4 and 7 days. The scaffolds were sectioned to disc weighing approximately 1.5 mg±0.2 and used for all cell culture studies.

Figure 7:
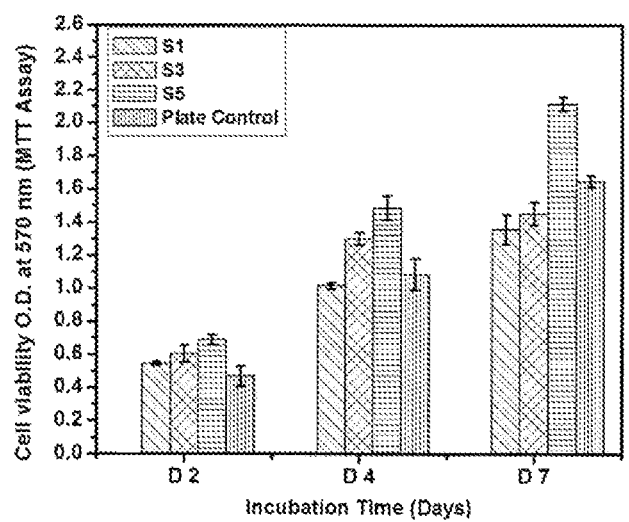
FIG. 7 depicts MTT assay showing fibroblasts exhibiting high metabolic activity cultured on three dimensional scaffold matrices for up to 7 days.
Figure 8:
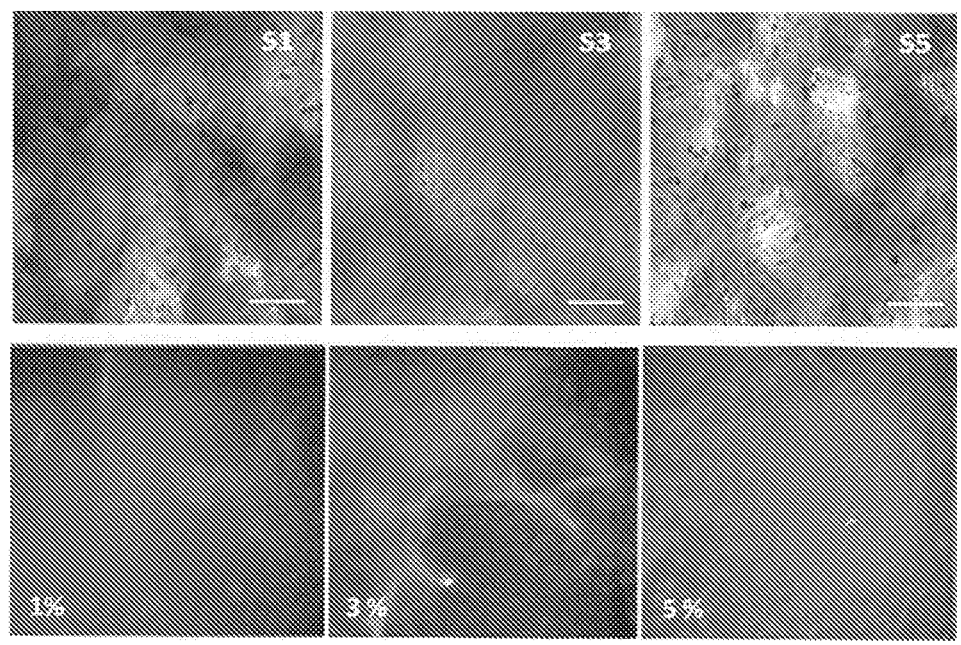

The cell viability at day 2, 4 and 7 by performing MTT assay is indicated in FIG. 7. The MTT profile demonstrated that scaffolds lack any adverse effect on cell growth and proved to be non-toxic. On day 7, significant difference in cellular activity as compared to the culture plate was found in S5 scaffolds. The sustained cellular activity exhibited by the results observed in FIG. 8 indicated that higher sophorolipid concentrations proved to aid in the enrichment for increased cellular activity. Cells migrate and distribute within scaffolds when observed on day 2 through confocal microscopy (FIG. 8).

ADVANTAGES OF THE INVENTION

The hydrogel composition synthesized using two different components i.e Silk fibroin and Sophorolipid is completely biocompatible as both the components are reported to be biocompatible and biodegradable and non-toxic. The gelation time is tunable.

The instant hydrogel composition is derived from naturally occurring proteinaceous biopolymer, silk fibroin, which mimics the advantageous feature of natural extracellular matrix, aids in cell viability, organization and proliferation and therefore can be employed as cell scaffold for tissue repair. The second component of hybrid hydrogel i.e. sophorolipid adds to these advantages as it possesses antimicrobial, anti-cancerous, cell-differentiation and apoptosis inducing properties.

The invention claimed is:

1. A biocompatible hydrogel composition consisting of a sophorolipid (SL) and a silk fibroin (SF) wherein the sophorolipid (SL) consists of sophorose and oleic acid, linolenic acid, linoleic acid or stearic acid, wherein the pH of the sophorolipid (SL) is in the range of pH 6-10, the concentration of the sophorolipid is in the range of 1 to 5% (w/v) and the concentration of the silk fibroin is in the range of 3 to 5% (w/v).

2. The composition as claimed in claim 1, wherein the ratio of sophorolipid (SL) to silk fibroin is in the range of 1:3 to 1.6:1.

3. The composition as claimed in claim 1, wherein the silk fibroin is regenerated silk fibroin (RSF).

4. The composition as claimed in claim 1, wherein the pore size of the hydrogel composition is in the range of 20 to 200 μm.

5. The composition as claimed in claim 1, wherein said composition is lyophilized to provide 3D silk fibroin-sophoroplipid (SF-SL) scaffolds.

6. A process for the preparation of the hydrogel composition as claimed in claim 1, the process comprising the steps of:
  i. treating silk fibroin solution with sophorolipid in a ratio ranging between 3:1 to 1:1.6 to obtain a mixture;
  ii. allowing the mixture as obtained in step (i) to stand till gelation for a period in the range of 100 to 1000 minutes to obtain the hydrogel composition,
wherein the sophorolipid comprises sophorose and oleic acid, linolenic acid, linoleic acid or stearic acid, and
wherein the process is performed in physiological conditions and at a pH ranging from pH 6 to 10.

7. The process as claimed in claim 6, wherein the concentration of silk fibroin is in the range of 3 g % to 5 g % (w/v).

8. The process as claimed in claim 6, wherein the concentration of sophorolipid is in the range of 1 g to 5 g % (w/v).

9. The process as claimed in claim 6, wherein the silk fibroin is regenerated silk fibroin (RSF).

10. The process as claimed in claim 6, wherein the process is performed in physiological conditions at pH 8.

11. The composition as claimed in claim 1, wherein the concentration of silk fibroin is 3 g % (w/v).

12. The process as claimed in claim 6, wherein the concentration of silk fibroin is 3 g % (w/v).

13. A method for preparation of a 3D scaffold using the biocompatible hydrogel composition as claimed in claim 1, wherein the method comprises:
  a) culturing the composition of claim 1 at a temperature of 25° C. in a cell culture plate; and
  b) lyophilizing the culture plate for at least 16 hours to obtain the 3D scaffold.

* * * * *